(12) United States Patent
Zhou

(10) Patent No.: US 9,597,346 B2
(45) Date of Patent: Mar. 21, 2017

(54) METHODS FOR REDUCING PROTEIN LEVELS IN A CELL

(75) Inventor: Pengbo Zhou, Princeton Junction, NJ (US)

(73) Assignee: Cornell University, Ithaca, NY (US)

(*) Notice: Subject to any disclaimer, the term of this patent is extended or adjusted under 35 U.S.C. 154(b) by 181 days.

(21) Appl. No.: 13/522,143

(22) PCT Filed: Jan. 17, 2011

(86) PCT No.: PCT/US2011/021475
§ 371 (c)(1),
(2), (4) Date: Sep. 28, 2012

(87) PCT Pub. No.: WO2011/088435
PCT Pub. Date: Jul. 21, 2011

(65) Prior Publication Data
US 2013/0011920 A1    Jan. 10, 2013

Related U.S. Application Data

(60) Provisional application No. 61/295,636, filed on Jan. 15, 2010.

(51) Int. Cl.
| | |
|---|---|
| *A61K 31/7052* | (2006.01) |
| *A61K 38/53* | (2006.01) |
| *C12N 9/00* | (2006.01) |
| *C12N 15/11* | (2006.01) |

(52) U.S. Cl.
CPC .......... *A61K 31/7052* (2013.01); *A61K 38/53* (2013.01); *C12N 9/93* (2013.01); *C12N 15/111* (2013.01); *C07K 2319/70* (2013.01); *C12N 2310/11* (2013.01); *C12N 2310/14* (2013.01); *C12N 2320/31* (2013.01)

(58) Field of Classification Search
USPC ......... 435/69.77, 183, 375, 91.1, 6.1, 91.31, 435/320.1, 352, 366; 514/1, 2, 44; 536/23.1, 23.4, 24.5
See application file for complete search history.

(56) References Cited

U.S. PATENT DOCUMENTS

| | | | |
|---|---|---|---|
| 5,093,246 | A | 3/1992 | Cech et al. |
| 5,166,320 | A | 11/1992 | Wu et al. |
| 6,395,713 | B1 | 5/2002 | Beigelman et al. |
| 6,447,796 | B1 | 9/2002 | Vook et al. |
| 7,223,556 | B1* | 5/2007 | Zhou et al. ............... 435/68.1 |
| 7,772,203 | B2 | 8/2010 | Zamore et al. |
| 7,838,664 | B2 | 11/2010 | Tuschl et al. |
| 7,855,152 | B2 | 12/2010 | Yanase et al. |
| 7,858,771 | B2 | 12/2010 | McSwiggen et al. |
| 2002/0130430 | A1 | 9/2002 | Castor |
| 2007/0042463 | A1* | 2/2007 | Reed et al. ............... 435/69.1 |
| 2009/0047675 | A1 | 2/2009 | Roberts et al. |
| 2009/0143285 | A1 | 6/2009 | Sueoka et al. |
| 2012/0252028 | A1* | 10/2012 | Shtulman et al. ........... 435/6.13 |

FOREIGN PATENT DOCUMENTS

| | | |
|---|---|---|
| JP | 1047381 A | 2/1989 |
| WO | 9106309 A1 | 5/1991 |
| WO | 9206180 A1 | 4/1992 |
| WO | 9219749 A1 | 11/1992 |
| WO | 9220316 A2 | 11/1992 |
| WO | 9222635 A1 | 12/1992 |
| WO | 9304701 A1 | 3/1993 |
| WO | 9316785 A1 | 9/1993 |
| WO | 0053722 A2 | 9/2000 |
| WO | 03046185 A1 | 6/2003 |
| WO | 03047518 A2 | 6/2003 |

OTHER PUBLICATIONS

Novina et al., 2002, Nature Medicine, advance online publication doi: 10.1038/nm725.
Gonzalez et al., 1999, Bioconjugate Chem., 10, 1068-1074.
Lasic et al. Chem. Rev. 1995, 95, 2601-2627.
Ishiwata et al., Chem. Pharm. Bull. 1995, 43, 1005-1011.
Lasic et al., Science 1995, 267, 1275-1276.
Oku et al., 1995, Biochim. Biophys. Acta, 1238, 86-90.
Mizuno et al., (1992)No Shinkei Geka 20:547 551.
Mizuno et al., (1992) Neurol. Med. Chir. 32:873 876.
J. Virol, 2001; 75: 7583-91.
Zagorski WA, Knudsen ES, Reed MF. Retinoblastoma deficiency increases chemosensitivity in lung cancer. Cancer Res 2007; 67: 8264-73.
Sdek et al. The Central Acidic Domain of MDM2 is critical in inhibition of retinoblastoma-mediated suppression of E2F and cell growth. J Biol Chem 2004; 279: 53317-22.
Lee et al., 2002, Nature Biotechnology, 19, 500.
Paul et al. 2002, Nature Biotechnology, 19, 505.
Miyagishi and Taira, 2002, Nature Biotechnology, 19, 497.
R. J. Mayer, Protein Degradation: The Ubiquitin-Proteasome System and Disease, vol. 4, Wiley-VCH, 2007.

(Continued)

*Primary Examiner* — Jane Zara
(74) *Attorney, Agent, or Firm* — Leason Ellis LLP

(57) ABSTRACT

The present invention provides a method of reducing levels of at least one target protein in a cell. The cell is contacted with a first agent and a second agent. The first agent reduces synthesis of the target protein, e.g., by reducing levels of the mRNA of the target protein or inhibits translation of the mRNA. The second agent accelerates degradation of the target protein. The first agent may contact the cell before, after or simultaneously with the second agent. The first agent and the second agent may be in separate delivery vehicles, or in a single delivery vehicle. The first agent may be an RNAi (RNA interference) molecule, such as a small interfering RNA (siRNA), a small hairpin RNA (shRNA) or a microRNA (miRNA). The second agent may be a chimeric polypeptide containing a ubiquitin ligase polypeptide and a target protein interacting domain. The ubiquitin ligase polypeptide can be an E3 ubiquitin ligase, including, but not limited to, an SCF polypeptide, a HECT polypeptide and a UBR1 polypeptide. In one embodiment, the SCF polypeptide is an F-box polypeptide.

11 Claims, 4 Drawing Sheets

(56) References Cited

OTHER PUBLICATIONS

C.M. Croce, Oncogenes and Cancer, N. Engl. J. Med. 2008; 358:502-511.
Hochstrasser, 1996 Annu Rev. Genet 30:405 39.
Zhou et al., Harnessing the ubiquitination machinery to target the degradation of specific cellular proteins. Mol. Cell. 2000; 6: 751-6.
Zhang et al. Exploring the functional complexity of cellular proteins by protein knockout. Proc Natl Acad Sci U.S.A. 2003; 100: 14127-32.
Zhang et al. Ectopic targeting of substrates to the ubiquitin pathway. Methods Enzymol 2005; 399:823-33.
Zhou P. Targeted protein degradation. Curr Opin Chem Biol 2005; 9: 51-5.
Cardozo et al., The SCF ubiquitin ligase: insights into a molecular machine. Nat Rev Mol Cell Biol. 2004 5 (9):739-51).
Verdel et al., 2004, Science, 303, 672-676.
Pal-Bhadra et al., 2004, Science 303, 669-672.
Allshire, 2002, Science, 297, 1818-1819.
Volpe et al., 2002, Science, 297, 1833-1837.
Jenuwein, 2002, Science, 297, 2215-2218.
Hall et al., 2002, Science, 297, 2232-2237.
Zamore P.D. Nature Structural Biology, 2001, 8 (9) 746-750.
Zamore et al, Cell, 101, 25-33, (2000).
Elbashir et al. Nature, 411, 494-498, (2001).
Fire (1999) Trends Genet, 15: 358-363.
Sharp (2001) Genes Dev. 15:485-490.
Hammond et al. (2001) Nature Rev. Genes 2: 1110-1119.
Tuschl (2001) Chem. Biochem. 2:239-245.
McIntyre G, Fanning G (2006). "Design and cloning strategies for constructing shRNA expression vectors". BMC Biotechnol. 6: 1.
Paddison P, Caudy A, Bernstein E, Hannon G, Conklin D (2002). "Short hairpin RNAs (shRNAs) induce sequence-specific silencing in mammalian cells". Genes Dev. 16(8): 948-58.
Bartel, DP (2009). "MicroRNAs: target recognition and regulatory functions." Cell, 2004, 136 (2):215-33.
Bartel, DR "MicroRNAs: genomics, biogenesis, mechanism, and function." Cell, 116 (2):281-97.
Rossi, J., 1994, Current Biology 4: 469-471.
Van Der Voorn and Ploegh (1992) FEBS Lett 307: 131 4.
Kamura et al. (1999) Science 284: 657-61.
Skowyra (1999) Science 284: 662-5.
Ohta et al., (1999) Mol Cell 3: 535-41.
Tan et al. (1999) Mol Cell 3: 527-33.
Huibegtse et al. (1995) Proc Natl Acad Sci USA 92: 2563 7.
Wang et al. (1999) Mol Cell Biol 19:342 52.
Zhu et al. (1999) Nature 400: 687 93.
Saleh et al. (1998) J Mol Biol 282: 933 46.
Utsugi et al. (1999) Gene 234: 285 95.
Callaghan et al. (1999) Oncogene 17: 3479 91.
Kwon et al. (1998) Proc Natl Acad Sci USA 95: 7893 903.
Varshavsky (1996) Proc Natl Acad Sci USA 93: 12142 9.
Margottin et al. (1998) Mol. Cell 1: 565.
Bai et al. (1996) Cell 86:263.
Kominami et al. (1997), Genes Dev. 11: 1548.
Li et al. (1997) EMBO J. 16:5629.
Skowyra et al. (1997) Cell 91:209.
Fields and Song (1989) Nature 340:245 6.
Gyuris et al. (1993) Cell 75:791 803.
Chien et al. (1991) Proc. Natl. Acad. Sci. (U.S.A.) 88: 9578 or Cell 72:233.
International Search Report and Written Opinion dated Mar. 9, 2011.

\* cited by examiner

A.

B.

A.

B.

METHODS FOR REDUCING PROTEIN LEVELS IN A CELL

CROSS REFERENCE TO RELATED APPLICATION

This application claims the benefit under 35 U.S.C. §119 (e) of U.S. Provisional Application No. 61/295,636, filed on Jan. 15, 2010.

FIELD OF THE INVENTION

The present invention relates to methods of reducing protein levels in a cell. In particular, the present invention relates to a method of reducing levels of a protein by simultaneously down-regulating synthesis of the protein (e.g., through reducing levels of its mRNA or reducing translation of its mRNA) and increasing degradation of the protein.

BACKGROUND OF THE INVENTION

Inappropriate activation of certain cellular proteins is associated with the development of various human disease, including cancer, cardiovascular, immunological and neurological diseases. R. J. Mayer, Protein Degradation: The Ubiquitin-Proteasome System and Disease, Volume 4, Wiley-VCH, 2007. For example, in many cancers, overexpression of one or more oncogenes plays a critical role in the initiation and progression of tumors. C. M. Croce, Oncogenes and Cancer, N. Engl. J. Med. 2008; 358:502-511. Therefore, an effective method to down-regulate the level of a target protein which causes or contributes to a disease would have significant diagnostic and therapeutic impacts. Additionally, different tools have been harnessed to reduce target protein levels in order to assess their biological functions.

RNA interference (RNAi), gene knockout, ribozymes and anti-sense oligonucleotides are frequently used in different eukaryotic organisms to eliminate or reduce the level of a cellular protein. However, in some cases, these techniques do not sufficiently ablate protein expression. Oftentimes, because existing gene products are removed only at the rate of their natural turnover, the immediate depletion of a target protein cannot be achieved. Another factor to consider is the stability of the target protein, which dictates the rate and, therefore, the efficiency of its depletion. Even if nascent mRNAs have been totally destructed, the residual long-lived target proteins may distort or obscure the assessment of the protein ablation phenotype.

Ubiquitin-dependent proteolysis is a major catabolic pathway utilized by eukaryotic cells for the degradation of cellular proteins. Protein ubiquitination is catalyzed by concerted actions of three classes of enzymes: the E1 ubiquitin-activating enzymes, the E2 ubiquitin-conjugating enzymes, and the E3 ubiquitin protein ligases (reviewed in Hochstrasser (1996) Annu Rev. Genet 30: 405 39). While E1 and E2 are primarily involved in the activation and transfer of ubiquitin, the substrate specificity of the ubiquitin pathway is conferred by the E3 ubiquitin protein ligases. Recently, we demonstrated that, through a technique we designated "protein knockout" (PKO), engineered ubiquitin ligases can be utilized to accelerate proteolysis of specific intracellular proteins. Zhou et al. Harnessing the ubiquitination machinery to target the degradation of specific cellular proteins. Mol. Cell. 2000; 6: 751-6. Zhang et al. Exploring the functional complexity of cellular proteins by protein knockout. Proc Natl Acad Sci USA 2003; 100: 14127-32. Zhang et al. Ectopic targeting of substrates to the ubiquitin pathway. Methods Enzymol 2005; 399: 823-33. Zhou P. Targeted protein degradation. Curr Opin Chem Biol 2005; 9: 51-5.

By combining RNAi and protein knockout techniques, the Applicant has further developed a method that reduces the amount of a target protein rapidly and effectively. RNAi operates at the level of protein biosynthesis via degradation of the specific mRNA or inhibition of its translation, while ubiquitin ligase-mediated protein knockout functions at the post-translational level to accelerate the degradation of the desired protein. This combination approach is generally applicable to any target protein, including proteins that cannot be sufficiently eliminated by RNAi, and proteins with a relatively long half-life.

SUMMARY OF THE INVENTION

It is an object of the present invention to provide for a method of reducing levels of at least one target protein in a cell comprising the step of contacting the cell with a first agent and a second agent, wherein the first agent reduces synthesis of the target protein, the second agent increases degradation of the target protein. The first agent may contact the cell before, after or simultaneously with the second agent. The first agent and the second agent may be in separate delivery vehicles, or may be in a single delivery vehicle.

The first agent may reduce levels of mRNA of the target protein or reduce translation of mRNA of the target protein. The first agent can be an RNAi molecule, such as a small interfering RNA (siRNA), a small hairpin RNA (shRNA), and a microRNA (miRNA). The first agent can also a double-stranded RNA (dsRNA), an antisense oligonucleotide, or a ribozyme.

The second agent may be a chimeric polypeptide comprising a ubiquitin ligase polypeptide and a target protein interacting domain. The ubiquitin ligase polypeptide can be an E3 ubiquitin ligase polypeptide, such as an SCF polypeptide, a HECT polypeptide and a UBR1 polypeptide. The SCF polypeptides include, but are not limited to, an F-box polypeptide, such as Cdc4/FBW7, HOS, βTrCP, FWD1, Pop1p, Pop2p, Grr1p and Met30p. The HECT polypeptides include, but are not limited to, E6AP, Nedd4, RSP5, Smurf1, TOM1 and EDD. Non-limiting examples of the target protein interacting domains include a papillomavirus E7 polypeptide and an SV-40 LTP polypeptide.

The present methods and compositions may be used to target any protein, including a cytoplasmic protein, a nuclear protein, or a membrane protein. For example, the target protein may be Rb, p107, IκB, Sic1p, Cln2p, E2, c-myc and β-catenin. The target protein may be in any type of cells, including a mammalian cell, such as a human cell or a murine cell.

The present invention can be used to treat or prevent a disease or condition (e.g., cancer or cardiovascular disease) in a subject. The present invention may also be used to diagnose a disease or condition in a subject.

Also encompassed by the present invention is an expression vector comprising a first nucleic acid sequence encoding a first agent and a second nucleic acid sequence encoding a second agent. The first agent reduces synthesis of a target protein; the second agent increases degradation of the target protein.

The present invention further provides for a cell comprising an expression vector, wherein the expression vector comprises a first nucleic acid sequence encoding a first agent and a second nucleic acid sequence encoding a second agent. The cell can be any type of cells including a mammalian cell, such a human cell or a murine cell. The present invention provides for a cell comprising a first expression vector and a second expression vector, wherein the first expression vector comprises a first nucleic acid sequence encoding a first agent, the second expression vector comprises second nucleic acid sequence encoding a second agent.

Encompassed in the invention is an article of manufacture comprising an expression vector, wherein the expression vector comprises a first nucleic acid sequence encoding a first agent and a second nucleic acid sequence encoding a second agent. In another embodiment, the present invention provides for an article of manufacture comprising a first expression vector and a second expression vector, wherein the first expression vector comprises a first nucleic acid sequence encoding a first agent, the second expression vector comprises a second nucleic acid sequence encoding a second agent. In a further embodiment, the present invention provides for an article of manufacture comprising a first agent and a second agent.

BRIEF DESCRIPTION OF THE DRAWINGS

FIG. 2A shows that the hybrid E3 ligase β-TrCP-E7N contains the β-TrCP F-box motif fused to the E7N peptide. The β-TrCP F-box motif facilitates interaction with the SCF core E3 ubiquitin ligase complex, and the E7N peptide binds Rb (as well as pocket proteins p107 and p130).

In FIG. 2B, SAOS-2 cells were transfected with constructs encoding anti-RB1 shRNA, β-TrCP-E7N or both anti-RB1 shRNA and β-TrCP-E7N. All samples were selected with puromycin 24 hrs post-transfection, then analyzed by immunoblotting with specific antibodies.

DETAILED DESCRIPTION OF THE INVENTION

Figure 1:
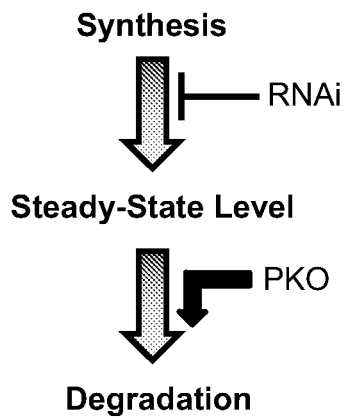
FIG. 1 depicts that integration of RNAi and protein knockout (PKO) achieves more effective and rapid reduction in target protein levels. RNAi reduces synthesis of the nascent target protein, while protein knockout accelerates degradation of the target protein.

The present invention takes advantage of both pre-translational and post-translational means to down-regulate levels of a target protein. The target protein level is effectively and rapidly reduced through decreased protein synthesis and increased protein degradation. The invention can be used to reduce the amount of a target protein to various extent as well as to eliminate all of the target protein in a cell. The present methods and compositions can be used to target essentially any protein. Importantly, the combination use of the first agent and second agent produces a synergistic effect that is much greater than the predicted additive effect based on the individual agents.

The present invention provides a method for reducing levels of at least one target protein in a cell. The method comprises the step of contacting the cell with a first agent and a second agent: the first agent reduces synthesis of the target protein; whereas the second agent reduces levels of the target protein. For example, the first agent may decrease levels of the mRNA of the target protein (e.g., by inducing degradation of the mRNA, or by down-regulating transcription of encoding gene of the target protein to reduce the mRNA level). The first agent may also reduce or inhibit translation of the mRNA. The second agent may accelerate degradation of the target protein. The first agent may contact the cell before, after or simultaneously with the second agent. The first agent and the second agent may be in separate delivery vehicles, or in a single delivery vehicle.

The first agent may be an RNAi (RNA interference) molecule, such as a small interfering RNA (siRNA), a small hairpin RNA (shRNA) or a microRNA (miRNA). The first agent may be a double-stranded RNA (dsRNA), an antisense oligonucleotide, a ribozyme, or a triple-helix DNA.

The second agent may be a chimeric polypeptide comprising a ubiquitin ligase polypeptide and a target protein interacting domain. This chimeric polypeptide comprising a ubiquitin ligase polypeptide and a target protein interacting domain is herein also referred to as an engineered ubiquitin ligase. The ubiquitin ligase polypeptide can be an E3 ubiquitin ligase including, but not limited to, an SCF polypeptide, a HECT polypeptide and a UBR1 polypeptide. In one embodiment, the SCF polypeptide is an F-box polypeptide, including, but not limited to, any member of the known F-box-containing substrate recognition subunit family of proteins in mammalian cells, such as Cdc4/FBW7, HOS, βTrCP and FWD1, or Pop1p, Pop2p, Grr1p and Met30p in lower eukaryotes (reviewed in Cardozo et al, The SCF ubiquitin ligase: insights into a molecular machine. *Nat Rev Mol Cell Biol.* 2004 5(9):739-51). The HECT polypeptides include, but are not limited to, E6AP, Nedd4, RSP5, Smurf1, TOM1 and EDD. The ubiquitin ligase polypeptide may be linked to the target protein interacting domain covalently or non-covalently. The technique of using this second agent to down-regulate a target protein level is herein also referred to as "protein knockout" ("PKO").

The invention also encompasses an expression vector comprising a first nucleic acid sequence encoding a first agent and a second nucleic acid sequence encoding a second agent as described above. Alternatively, the invention provides for a first expression vector comprising a first nucleic acid sequence encoding a first agent, and a second expression vector comprising a second nucleic acid sequence encoding a second agent. The vector may be a viral vector or a plasmid, particularly an expression vector suitable for expression in eukaryotic cells, including mammalian cells.

The invention can be used to reduce the amount of a target protein to various extent as well as to eliminate all of the target protein in a cell. Levels of a target protein reduced by the present invention may be greater than about 10%, greater than about 20%, greater than about 30%, greater than about 40%, greater than about 50%, greater than about 60%, greater than about 70%, greater than about 80%, greater than about 90%, or about 100%.

The present invention can be used to target any protein or polypeptide for which the encoding gene has been cloned (or partially cloned), or for which an interacting polypeptide (or domain) is known or can be elucidated by one of skill in the art. The terms "protein level(s)", "protein amount", "the amount of a protein" and "level(s) of a protein" can be used interchangeably herein.

RNAi operates at the biosynthesis level through degrading the mRNA of the target protein or decreases mRNA translation. However, the target protein is still being removed at a regular speed by the endogenous protein destruction machinery. The protein knockout system acts at the post-translational level to accelerate degradation of the target protein by the ubiquitin-proteasome pathway, but has a minimal effect on nascent protein synthesis. In certain embodiments, the present invention uses both RNAi and protein knockout to reduce levels of cellular proteins of interest. By combining these two technologies, more efficient and rapid depletion of the target protein may be achieved than either technology alone. Importantly, the combination of RNAi and protein knockout produces a synergistic effect that is much greater than the predicted additive effect based on the individual technologies.

First Agent: Pre-Translational Regulation

The first agent reduces levels of the mRNA of the target protein or reduces translation of the mRNA. The first agent can be RNA, DNA or nucleic acid analogs, including chemically modified nucleotides (e.g., sugar- or backbone-modified nucleotides) and non-nucleotides. Other nucleic analogs, such as peptide nucleic acids (PNA) or locked nucleic acids (LNA), are also suitable. U.S. Pat. No. 7,838,664. Chemical modification may improve various properties of native nucleic acid molecules through increased resistance to nuclease degradation in vivo and/or through improved cellular uptake. Furthermore, certain chemical modifications can improve the bioavailability of nucleic acid molecules by targeting particular cells or tissues and/or improving cellular uptake of the nucleic acid molecule. U.S. Pat. No. 7,858,771.

The first agent may be in single-stranded or double-stranded forms. The double-stranded nucleic acid molecules may have two blunt ends, one overhang and one blunt end, or both 3' and 5' overhangs. The double-stranded nucleic acid can comprise mismatches, bulges, loops, or wobble base pairs.

The first agent may be an RNAi molecule, such as a small interfering RNA (siRNA), a small hairpin RNA (shRNA) or a microRNA (miRNA). The first agent may be a double-stranded RNA (dsRNA), an antisense oligonucleotide, a ribozyme, or a triple-helix DNA.

The first agent of the invention may include one or more than one type of nucleic acid molecules having specificity towards a target protein. For example, only one type of siRNA may be used to down-regulate a target protein level; two types of siRNA (e.g., with different sequences) may be used in combination to modulate expression level of a target protein; an antisense oligonucleotide may be combined with an siRNA to reduce a target protein level.

The first agent of the invention down-regulates a target protein at various levels, such as post-transcriptional level, pre-transcriptional level, or epigenetic level. In a non-limiting example, epigenetic regulation of gene expression by RNAi molecules of the invention can result from RNAi mediated modification of chromatin structure to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

The first agent of the invention can be designed to target DNA or a variety of RNA molecules of the target protein. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention can be used to inhibit or reduce gene expression through the appropriate exons to specifically inhibit or to distinguish among the functions of gene family members. In another embodiment, the first agent is used to target conserved sequences corresponding to a gene family or gene families.

RNAi-mediated silencing is gene specific. RNAi is a two step process. First, dsRNA is cleaved within the cell to yield siRNAs with 5' terminal phosphate and 3' short overhangs. Secondly, the siRNAs specifically target the corresponding mRNA sequence for destruction. Zamore P. D. *Nature Structural Biology*, 2001, 8 (9) 746-750. RNAi may also be efficiently induced using chemically synthesized siRNA duplexes. Zamore et al, *Cell*, 101, 25-33, (2000). Synthetic siRNA duplexes have been shown to specifically suppress expression of endogenous and heterologous genes in a wide range of mammalian cell lines. Elbashir et al. *Nature*, 411, 494-498, (2001). Fire (1999) *Trends Genet.* 15: 358-363. Sharp (2001) *Genes Dev.* 15: 485-490. Hammond et al. (2001) *Nature Rev. Genes* 2: 1110-1119. Tuschl (2001) *Chem. Biochem.* 2: 239-245.

The RNAi molecule of the present invention can be double-stranded or single-stranded. When the RNAi is double-stranded, one strand is the sense strand and the other is the antisense strand; the antisense strand comprises nucleotide sequence that is complementary to the nucleotide sequence of a target protein or a portion thereof, and the sense strand comprises nucleotide sequence corresponding to the nucleotide sequence of a target protein or a portion thereof. Alternatively, the RNAi molecule is assembled from a single oligonucleotide, where the self-complementary sense and antisense regions of the RNAi molecule are linked by means of a nucleic acid-based or non-nucleic acid-based linker(s). The RNAi molecule can be a polynucleotide with a duplex, asymmetric duplex, hairpin or asymmetric hairpin secondary structure. The RNAi can be a circular single-stranded polynucleotide having two or more loop structures and a stem comprising self-complementary sense and antisense regions. The circular polynucleotide can be processed either in vivo or in vitro to generate an active RNAi molecule.

A small interfering RNA (siRNA) is a double-stranded RNA molecule that is capable of inhibiting or reducing the expression of a gene with which it shares homology. Each strand of the siRNA may be about 10 to about 50 nucleotides, about 12 to about 45 nucleotides, about 15 to about 40 nucleotides, about 20 to about 35 nucleotides, about 20 to about 30 nucleotides, or about 20 to about 25 nucleotides in length. The double stranded siRNA may have about 10 to about 50 base pairs, about 12 to about 45 base pairs, about 15 to about 40 base pairs, about 20 to about 35 base pairs, about 20 to about 30 base pairs, or about 20 to about 25 base pairs.

Several methods have been used to deliver siRNAs to cells. These methods include delivering synthetic siRNA molecules into cells, and vector-based methods in which siRNA is transcribed in a target cell by the vector. Certain vector-based siRNA delivery systems can result in persistent and effective suppression of gene expression. In many vector-based methods, the siRNA is generated by the production of small hairpin RNA or short hairpin RNA (shRNA). shRNA is a single-stranded RNA molecule comprising stem and hairpin structures. In such a system, an RNA polymerase III promoter, such as H1 promoter and U6 promoter, is used to drive transcription of shRNA. The shRNA is processed in the cell into siRNA through the action of the Dicer family of enzymes. Thus, the transcribed products mimic the synthetic siRNA duplexes and are effective for suppressing their corresponding genes. U.S. Pat. No. 7,772,203. McIntyre G, Fanning G (2006). "Design and cloning strategies for constructing shRNA expression vectors". *BMC Biotechnol.* 6: 1. Paddison P, Caudy A, Bernstein E, Hannon G, Conklin D (2002). "Short hairpin RNAs (shRNAs) induce sequence-specific silencing in mammalian cells". *Genes Dev.* 16 (8): 948-58. shRNAs may be about 30 to about 80 (e.g., about 35, 40, 45, 50 or 55) nucleotides, about 35 to about 70 nucleotides, about 35 to about 65 nucleotides, about 35 to about 60 nucleotides, about 35 to about 55 nucleotides, about 35 to about 50 nucleotides, or about 38 to about 44 (e.g., 38, 39, 40, 41, 42, 43 or 44) nucleotides in length. The double stranded region of the shRNA may have about 10 to about 35 base pairs, about 12 to about 30 base pairs about 14 to about 25 base pairs, or about 16 to about 22 (e.g., about 16, 17, 18, 19, 20, 21 or 22) base pairs.

The first agent may also be a microRNA (miRNA) molecule, analogs thereof, a miRNA precursor such as pre-miRNA and primary miRNA (pri-miRNA). The first agent may be DNA molecules encoding miRNA or miRNA precursor molecules. Bartel, D P (2009). "MicroRNAs: target recognition and regulatory functions". *Cell,* 2004, 136 (2): 215-33. Bartel D P. "MicroRNAs: genomics, biogenesis, mechanism, and function". *Cell,* 116 (2): 281-97. The miRNA is usually a single-stranded molecule, while the miRNA precursor is usually an at least partially self-complementary molecule capable of forming double-stranded portions, e.g. stem- and loop-structures.

The invention also relates to an expression vector encoding an miRNA-molecule or miRNA precursor molecule as described above. The vector can be a DNA vector, e.g. a viral vector or a plasmid, particularly an expression vector suitable for nucleic acid expression in eukaryotic, more particularly, mammalian cells. The recombinant nucleic acid contained in said vector may be a sequence which results in the transcription of the miRNA molecule, a precursor or a primary transcript thereof, which may be further processed to give the miRNA molecule.

Antisense oligonucleotides include DNA, RNA, or their derivatives, analogues, fragments, hybrids, mimetics, and congeners. Antisense oligonucleotides may prevent protein translation of a specific messenger RNA by binding to them. Antisense oligonucleotides may range from about 5 to about 10, about 10 to about 20, about 10 to about 40, about 15 to about 25, about 20 to about 50, about 50 to about 75, or about 75 to about 100 nucleotides in length. The target sequences may be RNA or DNA, and may be single-stranded or double-stranded. Target molecules include, but are not limited to, pre-mRNA, mRNA, and DNA.

Ribozymes are enzymatic RNA molecules capable of catalyzing the specific cleavage of RNA. (For review, see Rossi, J., 1994, *Current Biology* 4: 469-471.) The mechanism of ribozyme action involves sequence specific hybridization of the ribozyme molecule to complementary target RNA, followed by an endonucleolytic cleavage. The composition of ribozyme molecules must include one or more sequences complementary to the target mRNA, and may include the well known catalytic sequence responsible for mRNA cleavage. U.S. Pat. No. 5,093,246. Within the scope of the invention are engineered hammerhead motif ribozyme molecules that specifically and efficiently catalyze endonucleolytic cleavage of RNA sequences encoding target proteins. U.S. Pat. No. 7,855,152.

The first agent may be any small organic molecule that is able to reduce levels of the mRNA of the target protein or reduce translation of the mRNA. A "small organic molecule" refers to an organic molecule, either naturally occurring or synthetic, that has a molecular weight ranging from about 50 daltons to about 5000 daltons, from about 100 daltons to about 4000 daltons, from about 150 daltons to about 3000 daltons, from about 200 daltons to about 2500 daltons, from about 100 daltons to about 2000 daltons, from about 200 daltons to about 1000 daltons, or from about 100 daltons to about 500 daltons.

Second Agent: Post-Translational Regulation

The second agent of the present invention induces or promotes degradation of a target protein through recruitment of the target protein to a ubiquitin ligase.

The second agent allows a target protein to be recruited to E3 ubiquitin ligases, such as the SCF ubiquitin ligases, the HECT ubiquitin ligases, or the UBR1 ubiquitin ligases. The target protein may be a natural substrate of these ubiquitin ligases, or may not normally be targeted for degradation by ubiquitin conjugation in general or by an E3-type ubiquitin protein ligase of the invention in particular. U.S. Pat. No. 7,223,556 teaches methods for targeting proteolysis of a polypeptide by cis or trans association with a ubiquitin protein ligase. The target protein may be recruited to an E3 ubiquitin ligase complex either by covalent joining of the target protein to a component of the complex (cis targeting) or by noncovalent association of the target protein with a component of the complex (trans targeting). The invention thereby provides for the controlled degradation of any cellular protein for which the encoding gene has been cloned or for which an interacting polypeptide is known or can easily be elucidated by one of skill in the art.

The second agent may be a chimeric polypeptide (also referred to as "engineered ubiquitin ligase" herein) comprising two functional subunits. The first functional subunit is referred to as the "ubiquitin ligase polypeptide" and allows the chimeric polypeptide to be targeted into the ubiquitin-dependent proteolysis pathway. The second functional subunit is referred to as the "target protein interacting domain" and is capable of binding to the target protein. The target protein interacting domain recruits the target protein for degradation by the ubiquitin-dependent proteolysis pathway.

The functional subunits may be derived from naturally-occurring polypeptides or may be non-naturally occurring homologs thereof.

In one aspect of the invention, the invention provides for the cis targeting of a protein. In this aspect of the invention, the target protein may be joined to a component of an SCF (Skp1/Cull 1/F-box protein) which serves as an SCF recruitment domain. The SCF recruitment domain may be an F-box protein and the target protein is produced as an F-box fusion protein. In certain embodiments, the F-box polypeptide-target protein fusion protein includes a WD-40 polypeptide region such as provided by the WD repeats of Cdc4p or as can be obtained from a large family of proteins which contain WD repeat sequences (see e.g. van der Voorn and Ploegh (1992) FEBS Lett 307: 131 4).

Ubiquitin Ligase Polypeptide of the Second Agent

Among the subunits of the SCF (Skp1, cullin and F-box-containing proteins) ubiquitin ligase complex, Skp1 and cullin form a stable core complex that is shared by different F-box-containing proteins. The SCF complex interacts with E2 through the cullin subunit. There exist multiple F-box proteins that serve to recruit various target proteins to the core SCF complex for ubiquitination. Different F-box proteins share the common F-box domain for Skp1 binding, but utilize additional modular protein-protein interacting domains, such as WD40 or leucine-rich repeats (LRR), for binding distinct classes of substrates. Kamura et al. (1999) Science 284: 657-61; Skowyra (1999) Science 284: 662-5; Ohta et al. (1999) Mol Cell 3: 535-41; Tan et al. (1999) Mol Cell 3: 527-33.

The HECT domain ubiquitin ligases include mammalian E6AP and Nedd4, and yeast RSP5 (Huibegtse et al. (1995) Proc Natl Acad Sci USA 92: 2563 7; Wang et al. (1999) Mol Cell Biol 19: 342 52) as well as the more recently discovered HECT domain ubiquitin ligases such as mammalian Smurf1 (Zhu, et al. (1999) Nature 400: 687 93), yeast TOM1 (saleh et al. (1998) J Mol Biol 282: 933 46; Utsugi et al. (1999) Gene 234: 285 95), and human EDD (Callaghan et al. (1999) Oncogene 17: 3479 91).

The UBR1 N-end rule ubiquitin ligases are involved in the degradation of polypeptides with particular N-terminal amino acid residues. The UBR1 ubiquitin ligases bind to destabilizing target protein N-terminal residues and facilitate ubiquitination of the bound target (Kwon et al. (1998) Proc Natl Acad Sci USA 95: 7893 903; Varshaysky (1996) Proc Natl Acad Sci USA 93: 12142 9).

In one embodiment, the first functional unit of the second agent, i.e., ubiquitin ligase polypeptide, is derived from a polypeptide component of an E3 ligase which interacts with the target protein to be degraded. In other words, the ubiquitin ligase polypeptide is a domain of a substrate recognition component of an E3 ubiquitin ligase complex, which domain is sufficient for recruiting the substrate recognition component into the E3 ubiquitin ligase complex. Non-limiting examples of ubiquitin ligase polypeptide include Cdc4/FBW7, HOS, βTrCP, FWD1, Pop1p, Pop2p, Grr1p, Met30p, and homologs and portions thereof.

The ubiquitin ligase polypeptide may contain an F-box or a portion thereof sufficient for interaction with at least one other E3 ubiquitin ligase component. In an exemplary embodiment, the ubiquitin ligase polypeptide comprises at least the F-box from the human protein β-TrCP, or homologs or portions thereof. Margottin et al. (1998) Mol. Cell 1: 565. The ubiquitin ligase polypeptide may also be derived from the following F-box containing proteins: Cdc4p, Grr1p, Met30p, Cyclin F; Skp2p; Pop1; C02F5.7; F48E8.7; MD6; YJL149w; N0376; 9934.4; 8039.5; N1161; SconB; Scon-2; fim; UFO; C02F5.7; C14B1.3; C17C3.6; C26E6.5; F43C9/1; F48E8.7; K10B2.1; T01E8.4; ZK328.7; Ro3D7; MD6; p110SIII; and E3012.9K (see, e.g., Margottin et al., (1998) Mol. Cell 1: 565; Bai et al. (1996) Cell 86:263; Kominami et al. (1997), Genes Dev. 11: 1548; Li et al. (1997) EMBO J. 16:5629). Yet other F-box proteins from which portions can be used in the invention include any of the F-box containing proteins described in Bai et al., supra, or F-box containing proteins that have not been isolated yet. Such proteins can be isolated based on the sequence homology between the F-boxes, using methods known in the art. An alignment of the F-boxes indicates the position of conserved residues (see, e.g., Bai et al., supra).

The ubiquitin ligase polypeptide may contain one or more than one WD repeat from an E3 substrate binding component, or at least a portion thereof sufficient for interaction with at least one other E3 component. The number of WD repeats that must be included in a hybrid protein of the invention, as well as which portion of the repeats must be included, can be determined as described in Skowyra et al. (1997) Cell 91:209. The WD repeats may be from β-TrCP, S. cerevisiae Met30p, Neurospora crassa Scon2p and the Xenopus levi proteins. Margollis et al., supra.

In certain embodiments, the ubiquitin ligase polypeptide comprises both an F-box and at least one WD repeat, or portions thereof, sufficient for recruitment into an E3 ubiquitin ligase complex.

The portion of a substrate recognition component of an E3 ubiquitin ligase complex that is necessary and sufficient for recruitment into the E3 ubiquitin ligase complex can be determined by several methods well known in the art which do not require undue experimentations. U.S. Pat. No. 7,223,556.

Homologs of known substrate recognition subunits can be identified using methods known in the art. For example, homologs can be cloned by hybridization at moderate or high stringency. Homologs can also be cloned by PCR using a low annealing temperature of the primers, allowing for hybridization of the primers to nucleic acids allowing for mismatches.

Target Protein Interacting Domain of the Second Agent

The second functional subunit of the chimeric polypeptide of the invention is a target protein interacting domain. A "target protein interacting domain" refers to a polypeptide or peptidomimetic that is capable of binding to a target protein. The second functional subunit of the chimeric polypeptide is a domain allowing the recruitment of a target protein to an E3 complex in a cell, to thereby degrade the target protein by the ubiquitin proteolytic pathway.

The target protein interacting domain can be, for example, a portion of a polypeptide that is known to interact with the target protein, or it can be a natural or synthetic polypeptide that has been identified by its ability to interact with the target protein.

The target protein interacting domains may be readily obtained by screening a library of naturally-occurring polypeptide sequence such as by using the yeast two-hybrid or "interaction trap" methodology (Fields and Song (1989) Nature 340:245 6; Gyuris et al. (1993) Cell 75:791 803). Yeast two-hybrid systems may be used to screen a mammalian (e.g., human) cDNA expression library, wherein a cDNA is fused to a GAL4 DNA binding domain or activator domain, and a nucleic acid encoding a polypeptide of interest, such as a target polypeptide, is fused to a GAL4 activator domain or DNA binding domain, respectively. Such a yeast two-hybrid system can screen for cDNAs encoding proteins which bind to polypeptides of interest.

For example, a cDNA library can be produced from mRNA from a cell line that expresses the target protein. Such a cDNA library cloned in a yeast two-hybrid expression system (Chien et al. (1991) *Proc. Natl. Acad. Sci.* (U.S.A) 88: 9578 or Cell 72: 233) can be used to identify cDNAs which encode proteins that interact with the target polypeptide and thereby produce expression of the GAL4-dependent reporter gene.

Alternatively, synthetic interacting domains may be obtained by any of various peptide display selection methods, such as phage display, which are known in the art. Other techniques include mammalian two-hybrid, Far Western, protein trap plus nucleic acid "snag" methods, surface plasmon resonance-based biomolecular interaction analysis methods, and polypeptide matrix display technologies. U.S. Pat. No. 7,223,556.

Polypeptides which interact with the target protein can also be identified by immunoprecipitation of a target protein with antibodies and identification of co-precipitated species. Further, polypeptides that bind the target protein can be identified by cross-linking in vivo with bi-functional cross-linking reagents and subsequent isolation of cross-linked products that include a target protein.

The target protein interacting domain may also be an antibody against the target protein or fragment of the antibody. The antibody may be an intact antibody, or an antibody fragment (e.g., Fab, nanobodies). The antibody or fragment thereof may contain one or more polypeptides. The antibodies may be types IgA, IgG, IgE, IgD or IgM (as well as subtypes thereof), wherein the light chains of the immunoglobulin may be of types kappa or lambda. The complementarity determining regions (CDRs) of the antibodies can be from a human or non-human source. The framework of the antibodies can be human, humanized, or non-human, e.g., a murine framework modified to decrease antigenicity in humans, or a synthetic framework, e.g., a consensus sequence.

Target protein interacting domains include, but are not limited to, a papillomavirus E7 polypeptide and an SV-40 LTP polypeptide.

Delivery of the First Agent and Second Agent

The first agent of the invention may be introduced into a cell as DNA or RNA molecules capable of reducing the translation of mRNA of a target protein or reducing levels of the mRNA of a target protein. The first agent may also be expressed from DNA or RNA expression vectors introduced into a cell.

The second agent of the invention may be introduced directly into a cell as a protein or polypeptide. The second agent may also be introduced as a nucleic acid encoding the second agent. For example, the second agent may be expressed from DNA or RNA expression vectors delivered into a cell.

To introduce the first agent and second agent into a cell, the two agents may be delivered simultaneously, e.g., in a single delivery vehicle. One embodiment of the invention provides an expression vector comprising a first nucleic acid sequence encoding the first agent and a second nucleic acid sequence encoding the second agent. For example, a single expression vector is used to simultaneously introduce both the protein knockout agent coding sequence (e.g., the engineered ubiquitin ligase expression cassette under the control of a Pol II promoter) and the shRNA coding sequence (under the control of a Pol III promoter) into a cell for expression of both agents.

Alternatively, the two agents may be delivered separately, e.g., in two separate delivery vehicles. For example, the RNAi and protein knockout agents can be introduced into the same target cells either individually in two independent expression vectors or simultaneously in the same expression vector. The first agent may be introduced into a cell as an shRNA, while the second agent may be introduced into the same cell in a polypeptide form. The first agent may contact the cell before, after or simultaneously with the second agent.

In one embodiment, an RNAi agent and a protein knockout agent are delivered into a cell individually. The RNAi agent is delivered either as a synthetic siRNA or in a vector as an shRNA expressed from a Pol III promoter (U6 or H1 promoters). Synthetic siRNAs can be transfected into target cells using the standard transfection reagents that are commercially available, including Lipofectamine RNAiMAX (Invitrogen) or DharmaFECT (Thermo Scientific Dharmacon). shRNAs can be delivered using either standard plasmid vectors (e.g. pSUPER) or viral-based vectors (e.g. adenoviral, retroviral or lentiviral vectors).

Protein knockout agents can be transfected into cells either as an expression plasmid, or can be introduced into cells by infection of viral (e.g., adenoviral, retroviral or lentiviral) vectors. Alternatively, protein knockout agents may be introduced into cells in protein forms. In this case, protein knockout agents (e.g., a chimeric polypeptide including a ubiquitin ligase polypeptide and a target protein interacting domain) can be expressed and purified from bacterial or insect (e.g., baculoviral) systems as protein forms. For delivery into a cell, the second agent may be fused to a membrane-transducing peptide, for example, derived from the HIV 1 TAT or from the homeodomain of vertebrate transcription factors. Purified second agent in a protein form can also be delivered into target cells directly using various delivery agent, including, but not limited to, the PROFECT protein delivery reagent (Targeting Systems) or ProteoJuice™ protein transfection reagent (Novagen).

In one embodiment, the first agent, such as siRNA or shRNA vectors, is transfected into the cell prior to transduction of the same cells with viral vectors encoding the second agent (e.g., a chimeric polypeptide comprising a ubiquitin ligase polypeptide and a target protein interacting domain) or delivery of the purified second agent proteins directly.

The expression vectors can be DNA plasmids or viral vectors. The vector may be a eukaryotic expression vector. The vector may contain a promoter, enhancer or other regulatory elements. The promoter may or may not be cell-type specific. The promoter can be constitutive or inducible. An inducible promoter is useful in embodiments in which the target protein is to be degraded in a controllable manner. Viral vectors can be constructed based on, but not limited to, adenovirus, adeno-associated virus, retrovirus, lentivirus or alphavirus.

Suitable expression vectors include pBR322-derived plasmids, pEMBL-derived plasmids, pEX-derived plasmids, pBTac-derived plasmids and pUC-derived plasmids for expression in prokaryotic cells, such as *E. coli*. Non-limiting examples of such expression vectors are described in Paul et al., 2002, *Nature Biotechnology*, 19, 505; Miyagishi and Taira, 2002, *Nature Biotechnology*, 19, 497; Lee et al., 2002, *Nature Biotechnology*, 19, 500; and Novina et al., 2002, *Nature Medicine*, advance online publication doi: 10.1038/nm725. For other suitable expression systems for both prokaryotic and eukaryotic cells, see Molecular Cloning A Laboratory Manual, 2.sup.nd Ed., ed. by Sambrook, Fritsch and Maniatis (Cold Spring Harbor Laboratory Press: 1989) Chapters 16 and 17.

The first agent and/or second agent may also be obtained by chemical synthesis methods.

The first agent and second agent may target the same pool of proteins or different subpopulations of the same protein. For example, protein knockout may only induce the degradation of a subpopulation of post-translationally modified protein, or the degradation of a subpopulation of target proteins localized to a specific subcellular compartment, whereas RNAi inhibits or reduces the translation of the mRNA of the target protein in general. Protein knockout may also be able to reduce the level of an entire family of target proteins with redundant function, of evolutionarily conserved proteins across different eukaryotic species.

Another embodiment of the invention provides a cell comprising an expression vector which has a first nucleic acid sequence encoding the first agent and a second nucleic acid sequence encoding the second agent. Also encompassed by the present invention is a cell comprising a first expression vector encoding the first agent and a second expression vector encoding the second agent. The first agent and second agent may be expressed in the cell conditionally (e.g., by using an inducible system), or may be expressed constitutively. The nucleic acid sequences encoding the first agent and/or the second agent may or may not be stably integrated into the cell's genome. The cell can be any eukaryotic cells, including, but not limited to, mammalian cells. The cell may be a human, murine, rat, canine, feline, bovine, ovine, porcine, goat, equine, primate, or yeast cell. The cell may be differentiated or undifferentiated, for example, a stem cell, embryonic stem cell, oocyte or embryonic cell.

The invention further provides for transgenic organisms including, but not limited to, transgenic plants and animals. The transgenic organism may comprise an expression vector which has a first nucleic acid sequence encoding the first agent and a second nucleic acid sequence encoding the second agent. The transgenic organism may comprise a first expression vector encoding the first agent and a second expression vector encoding the second agent.

These transgenic organisms can be used for a variety of purposes, e.g., to study the function of a target protein, to determine whether the absence of the target protein will result in a specific phenotype, such as the development of a specific disease.

The present compositions can be introduced into a cell by a variety of methods known to those of skill in the art, including, but not limited to, encapsulation in liposomes, iontophoresis, incorporation into other vehicles, such as biodegradable polymers, hydrogels, cyclodextrins (see for example Gonzalez et al., 1999, *Bioconjugate Chem.*, 10, 1068-1074; WO 03/47518 and WO 03/46185), poly(lactic-co-glycolic)acid (PLGA) and PLCA microspheres (see for example U.S. Pat. No. 6,447,796 and U.S. Patent Publication No. US 2002130430), biodegradable nanocapsules, and bioadhesive microspheres, or by proteinaceous vectors (WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. Alternatively, the nucleic acid/vehicle combination is locally delivered by direct injection or by use of an infusion pump.

The invention also features the delivery of the composition by surface-modified liposomes containing poly(ethylene glycol) lipids (PEG-modified, or long-circulating liposomes or stealth liposomes). Lasic et al. *Chem. Rev.* 1995, 95, 2601-2627; Ishiwata et al., *Chem. Pharm. Bull.* 1995, 43, 1005-1011. Lasic et al., *Science* 1995, 267, 1275-1276; Oku et al., 1995, *Biochim. Biophys. Acta,* 1238, 86-90).

In one embodiment, nucleic acids can be entrapped in liposomes bearing positive charges on their surface (e.g., lipofectins) and (optionally) which are tagged with antibodies against cell surface antigens of the target tissue (Mizuno et al., (1992) No Shinkei Geka 20:547 551; WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al., (1992) Neurol. Med. Chir. 32:873 876).

In yet another illustrative embodiment, the delivery system comprises an antibody or cell surface ligand which is cross-linked with a nucleic acid binding agent such as poly-lysine (see, for example, WO93/04701, WO92/22635, WO92/20316, WO92/19749, and WO92/06180). For example, any of the nucleic acids can be used to transfect specific cells in vivo using a soluble polynucleotide carrier comprising an antibody conjugated to a polycation, e.g. poly-lysine (see U.S. Pat. No. 5,166,320).

The introduction of the second agent to a cell may be through liposomal derived systems, poly-lysine conjugates, internalizing peptides, an artificial viral envelopes, protein carriers known to cross cell membranes.

Target Protein

A wide variety of proteins or polypeptides can be targeted using the present methods or compositions. The target protein may be a membrane protein, a nuclear or a cytoplasmic protein. The target protein may be involved in proliferation, immune response, inflammatory response, homing, cytotoxicity, clotting or dissolving of clots, hormonal regulation, etc. The protein may be naturally-occurring proteins, or mutants of naturally-occurring proteins.

Membrane proteins include receptors (e.g, growth factor receptors, cytokine receptors, interleukin receptors, G protein-coupled receptors), channel proteins, carrier proteins, proteins mediating apoptosis (e.g., Fas receptor), homing receptors, blood-related proteins, etc.

Intracellular proteins include proteins in metabolic pathways, regulatory proteins, steroid receptors, transcription factors, etc., depending upon the nature of the host cell. Some of the proteins indicated above can also serve as intracellular proteins.

In one embodiment, the target protein is involved in regulating the growth and/or differentiation and/or death of a cell. For example, the target protein can be an oncoprotein, the presence of which contributes to the immortalization of a cell. Accordingly, the invention provides methods and compositions for treating cancer and other proliferative disorders.

In another embodiment, the target protein is that of a microorganism, e.g., a virus, bacterium and fungus. The target protein may be a protein or polypeptide of an intracellular parasite or other intracellular pathogen. The target protein or polypeptide may be those which are necessary for the survival and/or reproduction of the microorganism. Thus, methods involving degradation of such polypeptides can be used for treating and/or preventing infections by microorganisms.

Non-limiting examples of target proteins include Rb, p107, IκB, Sic1p, Cln2p, E2, c-myc and β-catenin See PCT/US93/01617 for other candidate target proteins.

The cell into which the present compositions are introduced can be a cultured cell or can be part of a tissue or organ. The cell can be an undifferentiated cell, e.g., a blast cell, or the cell can be a differentiated or partially differentiated cell. The cell can be a somatic cell or a germ cell. The cell can be a normal cell or a cell from a tumor, e.g., malignant or benign tumor. The cell can be a blood cell, such as a lymphocyte, a granulocyte, an eosinophil, a basophil, an erythrocyte. In other embodiments, the cell can be a muscle cell, a renal cell, a liver cell, a epithelial cell, a bone cell (e.g., osteoblast or osteocyte), a cartilage cell, mesenchymal cell, endothelial cell, brain cell, or any other cell type, so long as the cell contains the necessary elements of the ubiquitin proteolysis pathway, or can be modified to contain these components.

The target cell can be any type of eukaryotic cell, present in a subject or outside of a subject. For example, the cell in which a target protein is to be degraded can be in a subject, and the first agent and second agent are administered to the subject. Alternatively, the cell can be obtained from a subject. The first agent and second agent are introduced into the cell, and the cell is optionally administered to the same or another subject. The cell can be a cell from any established cell line, which can be obtained, e.g., from the American Type Culture Collection (12301 Parklawn Drive, Rockville, Md.). The target cell can be any eukaryotic cells, including, but not limited to, mammalian cells. The cell may be a human, murine, rat, canine, feline, bovine, ovine, porcine, goat, equine, primate, or yeast cell.

The present methods and compositions may also be used in a cell-free system.

Pharmaceutical Compositions

The first agent and the second agent can be included in a pharmaceutical composition. The expression vectors for the first agent and second agent, or cells carry nucleic acid sequences encoding the first agent and second agent, may be included in a pharmaceutical composition.

To prepare such pharmaceutical compositions, the present molecules/compounds may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

The pharmaceutical compositions of the invention can be formulated for systemic and topical or localized administration. Systemic administration includes intramuscular, intravenous, intraperitoneal, and subcutaneous injection. For injection, the pharmaceutical compositions of the invention can be formulated in liquid solutions, for example, in physiologically compatible buffers such as Hank's solution or Ringer's solution. In addition, the pharmaceutical compositions may be formulated in solid form and redissolved or suspended immediately prior to use. Lyophilized forms are also included.

The present composition may be administered by any method known in the art, including, without limitation, intranasal, oral, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, transdermal, rectal, sub-lingual, mucosal, ophthalmic, spinal, intrathecal, intra-articular, intra-arterial, sub-arachnoid, bronchial and lymphatic administration. Topical formulation may be in the form of gel, ointment, cream, aerosol, etc; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

Kits

Also encompassed by the present invention is an article of manufacture comprising an expression vector having a first nucleic acid sequence encoding a first agent and a second nucleic acid sequence encoding a second agent. The first agent reduces levels of mRNA of a target protein or reduces translation of mRNA of the target protein; the second agent reduces levels of the target protein. The article of manufacture may also contain printed matter indicating that the expression vector is used to reduce levels of the target protein in a cell.

In another embodiment, the present invention provides an article of manufacture comprising a first expression vector encoding a first agent, and a second expression vector encoding a second agent. The first agent reduces levels of mRNA of a target protein or reduces translation of mRNA of the target protein; the second agent reduces levels of the target protein. The article of manufacture may also contain printed matter indicating that the expression vectors are used to reduce levels of the target protein in a cell.

In yet another embodiment, the present invention provides an article of manufacture comprising a first agent and a second agent. The first agent reduces levels of mRNA of a target protein or reduces translation of mRNA of the target protein; the second agent reduces levels of the target protein. The article of manufacture may also contain printed matter indicating that the first agent and second agent are used to reduce levels of the target protein in a cell.

The article of manufacture may be a kit. The kit can be used to down-regulate levels of a target protein in a biological system, including, for example, in a cell, tissue, or organism. The present invention can be used alone or as a component of a kit having at least one of the reagents necessary to carry out the in vitro or in vivo introduction of the current compositions to test samples and/or subjects. For example, components of the kit may include an expression vector of the invention and a vehicle that promotes introduction of the expression vector into cells of interest as described herein (e.g., using lipids and other methods of transfection known in the art, see, for example, U.S. Pat. No. 6,395,713).

The compositions may be presented in a pack or dispenser device. The pack may for example comprise metal or plastic foil, such as a blister pack. The pack or dispenser device may be accompanied by instructions for usage or administration. The kit may further comprise additional nucleic acids such as specialized vectors which contain at least one cloning site for insertion of a desired gene.

The instant invention provide useful compositions and methods for a variety of therapeutic, diagnostic, target validation, genomic discovery, genetic engineering, and pharmacogenomic applications. For example, when an abnormal amount of a specific protein causes or contributes to a disease or condition in a subject, the present methods and compositions may be used to treat or prevent the disease or condition, alone or in conjunction with one or more other therapeutic compounds. For example, the invention provides useful compositions and methods to treat cancer or cardiovascular diseases. In another embodiment, the invention features a method for diagnosing a disease or condition in a subject comprising administering to the subject a composition of the invention under conditions suitable for the diagnosis of the disease or condition in the subject.

The present methods and compositions can be used in combination with one or more known therapeutic agents to treat a disease or condition. Non-limiting examples of other therapeutic agents that can be readily combined with the methods and compositions of the invention are chemical compounds, enzymes, antibodies such as monoclonal antibodies, small molecules, and other organic and/or inorganic compounds including metals, salts and ions.

The invention provides a quick, easy, and economic alternative to the gene knock-out technology to eliminate any cellular protein in tissue culture or in animals. For example, a first agent and second agent or nucleic acids encoding such can be introduced into embryonic stem cells or in a blastocyst (for preparing transgenic animals), but also at any later stage of development of the embryo or animal, or even in an adult animal. Thus, the target protein can be degraded from the early developmental stages on, or it can be degraded only at specific developmental stages or in a mature animal. This allows the study of the function of a specific target protein, by specifically eliminating the polypeptide in the desired cell or in all the cells of an animal.

The following example is offered to illustrate, but not to limit, the claimed invention.

Example 1

Figure 2:
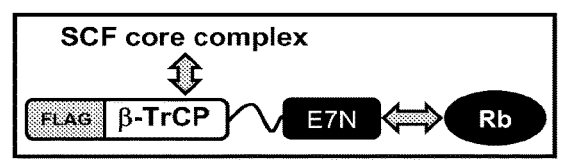
FIGS. 2A and 2B show that the combination of RNAi and protein knockout reduces ectopically expressed Rb level in the human osteosarcoma SAOS-2 cells more effectively than either method alone.
Figure 2:
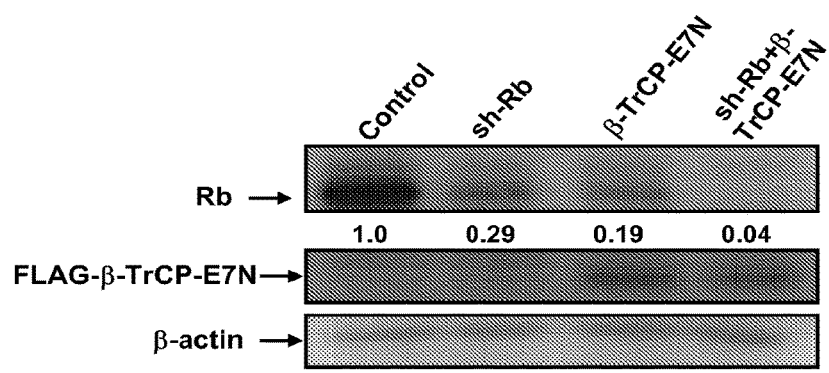

Targeted Degradation of the Retinoblastoma (Rb) Tumor Suppressor in Mammalian Cells Previously, we demonstrated that knockdown of Rb, a protein that possesses a relatively long half-life of 9 hrs, can be achieved at the post-translational level through directly accelerated ubiquitin-mediated proteolysis. Gonzalez et al. Degradation of the retinoblastoma tumor suppressor by the human papillomavirus type 16 E7 oncoprotein is important for functional inactivation and is separable from proteasomal degradation of E7. *J. Virol.* 2001; 75: 7583-91. Zhou et al. Harnessing the ubiquitination machinery to target the degradation of specific cellular proteins. *Mol. Cell.* 2000; 6: 751-6. Zhang et al. Exploring the functional complexity of cellular proteins by protein knockout. *Proc Natl Acad Sci USA* 2003; 100: 14127-32. Briefly, we constructed a hybrid E3 ligase that is able to recruit Rb to the CULL-based Skp1, Cull, and F-box-containing substrate receptor (SCF) ubiquitin ligase complex, and facilitate Rb polyubiquitination and its subsequent proteolysis (FIG. 2A). In doing so, we demonstrated that it is possible to engineer RING family ubiquitin ligases (such as the SCF complex) to recruit, ubiquitinate and induce proteolysis of specific intracellular proteins using a technique we designated "protein knockout" (PKO). Zhang et al. Ectopic targeting of substrates to the ubiquitin pathway. *Methods Enzymol* 2005; 399: 823-33. Zhou P. Targeted protein degradation. *Curr Opin Chem Biol* 2005; 9: 51-5.

Here, we posit that higher protein ablation can be achieved in a shorter period of time by combining the post-translational PKO system with transcript-targeting RNAi (FIG. 1). To test this two-pronged or double knock-down method, we utilized an anti-RB1 shRNA construct (Zagorski W A, Knudsen E S, Reed M F. Retinoblastoma deficiency increases chemosensitivity in lung cancer. *Cancer Res* 2007; 67: 8264-73), as well as the β-TrCP-E7N construct to target ectopically expressed Rb in SAOS-2 cells.

SAOS-2 cells were transfected by nucleofection (Amaxa) with pcDNA3-Rb-HA, and either pMSCV-LMP-sh-Rb encoding shRNA against Rb, pcDNA3-β-TrCP-E7N encoding β-TrCP-E7N or both. Control cells were transfected with pMSCV-LMP. All samples were selected with puromycin 24 hrs post-transfection, then analyzed by immunoblotting with antibodies against Rb, FLAG or β-actin.

As shown in FIG. 2B, either sh-Rb (i.e., shRNA against Rb) or β-TrCP-E7N alone were able to reduce Rb expression levels to 29% and 19% (relative to control), respectively, by 48 hrs. Introduction of both sh-Rb and PKO constructs resulted in nearly total elimination of Rb expression (with only 4% Rb remaining), surpassing the reduction seen in either shRNA or PKO constructs alone (FIG. 2B). Therefore, these results confirm that the combination approach is synergistically more effective than using either a post-transcriptional or post-translational technique alone.

Figure 3:
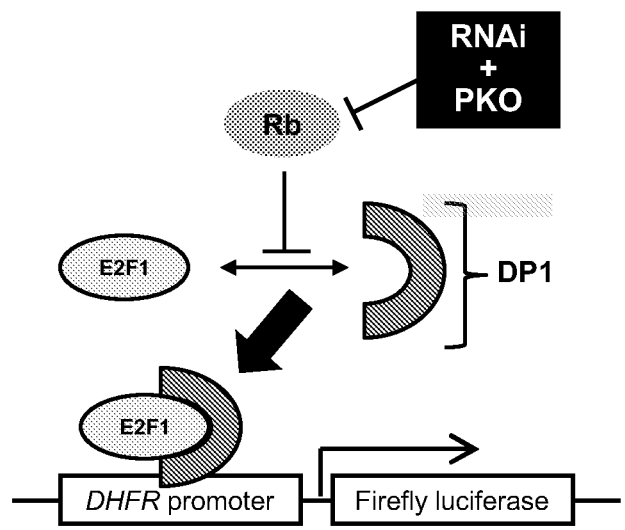
FIG. 3A demonstrates the functional analysis of the combination of RNAi and protein knockout in reducing cellular Rb level. E2F1, along with its cofactor DP-1, binds the DHFR promoter. Rb is able to inhibit E2F1 transcriptional activity. A luciferase reporter gene construct that is driven by the E2F1-responsive DHFR promoter (DHFR-luc) was used to study the effect of reduced Rb level.
FIG. 3B shows the dual-luciferase assay results of the combination use of RNAi and protein knockout in reducing cellular Rb level. SAOS-2 cells were transiently transfected with constructs encoding shRb (i.e., shRNA against Rb) and/or β-TrCP-E7N together with the DHFR-Luc reporter. The ratio of Firefly/Renilla (F/R) luciferase signal was measured in triplicate. Measurements were normalized to control and the graph indicates average (of three experiments) fold difference in F/R ratio. *indicates p-value <0.05.
Figure 3:
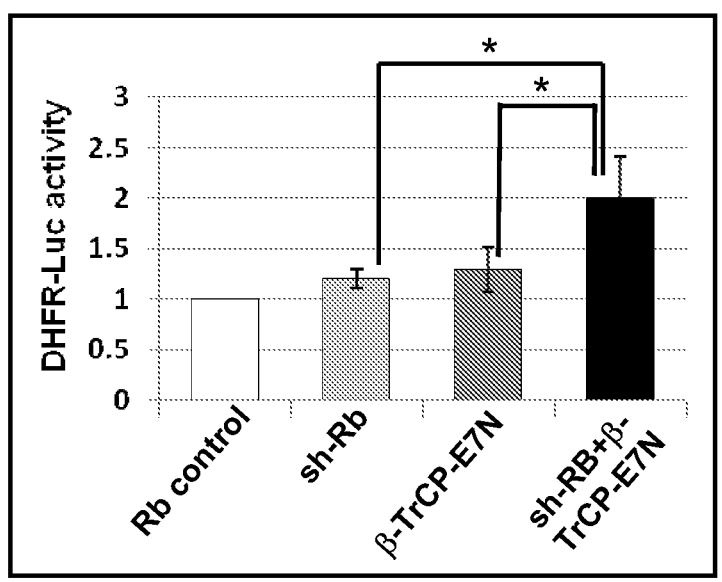

We next compared the single and combined knockdown techniques in their ability to disrupt an established cellular function of Rb in inhibiting E2F1 transcriptional activity. Here, we utilized a luciferase reporter gene construct driven by the E2F1-responsive DHFR promoter (DHFR-Luc) (FIG. 3A). Sdek et al. The central acidic domain of MDM2 is critical in inhibition of retinoblastoma-mediated suppression of E2F and cell growth. *J Biol Chem* 2004; 279: 53317-22. Dual-luciferase assay (Promega) was performed by first transfecting SAOS-2 cells with pcDNA3-Rb-HA, pcDNA-E2F1, pCMV-DP1, DHFR-luc, pRL-Tk (Renilla) and the indicated knockdown constructs. Cells were lysed after 24 hrs of puromycin selection, and the ratio of Firefly/Renilla (F/R) luciferase signal was measured in triplicate. Measurements were normalized to control and the graph indicates average (of three experiments) fold difference in F/R ratio.

In FIG. 3B, while single knockdown only yielded a relatively modest increase (20-30%) that is not statistically significant, the combination approach led to a synergistic de-repression of the DHFR promoter activity (an around two-fold increase), which is statistically significant ($p<0.05$). Thus, the effects of integrated RNAi and PKO also synergistically exceed either method alone from a functional perspective.

Example 2

Targeted Degradation of Endogenous p107 in Mammalian Cells

To assess the kinetic rate of target depletion by the combined RNAi and PKO technique, and also to demonstrate the versatility of the technique, we next targeted endogenous p107 protein. p107 is a member of the Rb family of tumor suppressors and also capable of binding HPV16 E7. C33A cells were transfected with anti-RBL1 siRNA oligonucleotides to target p107 transcript (Thermo Scientific), then infected with adenovirus bearing the β-TrCP-E7N construct. Average p107 expression levels were obtained from three separate experiments, and normalized to p107 levels in C33A cells that were mock transfected and infected.

Figure 4:
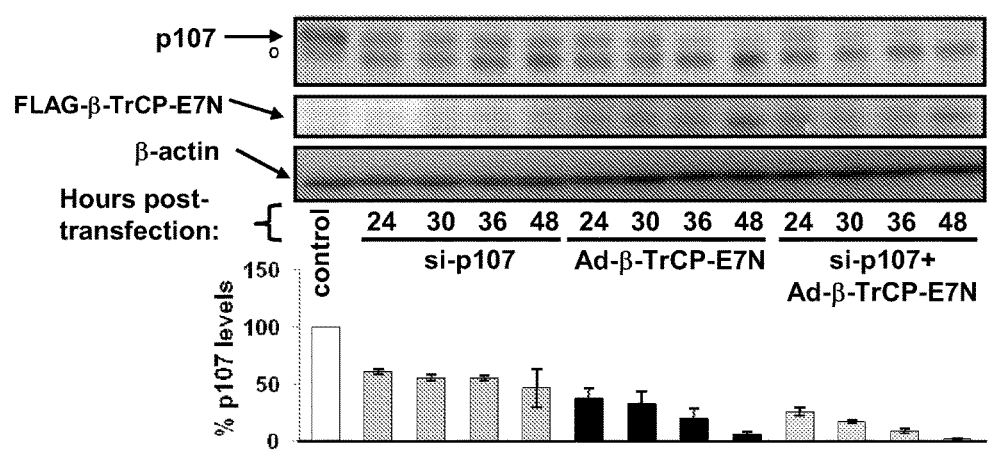
FIG. 4 shows the kinetic rate of eradicating endogenous p107 protein by the technique combining RNAi and protein knockout. C33A cells were transfected with anti-RBL1 siRNA oligonucleotides, then infected with adenovirus bearing the Ad1-β-TrCP-E7N construct. "o" indicates non-specific species. For the bar graphs, average p107 expression levels were obtained from three separate experiments, and normalized to p107 levels in C33A cells that were mock transfected and infected. Cells treated with both siRNA and Ad1-β-TrCP-E7N had the greatest level of p107 knockdown at all time points compared to either method alone.

Cells treated with both siRNA and Ad1-β-TrCP-E7N had the greatest extent of p107 knockdown at all time points compared to either method alone. Relative to the untreated control, the siRNA-transfected samples showed a 39% reduction in p107 expression at 24 hrs and reached 53% reduction by 48 hrs (FIG. 4). Ad1-β-TrCP-E7N-infected samples showed more marked p107 depletion than the siRNA-transfected samples with 62% and 94% reduction at 24 and 48 hrs, respectively. Strikingly, the siRNA plus Ad1-β-TrCP-E7N samples achieved the greatest extent of p107 knockdown at all time points, with 73% reduction in p107 levels at 24 hrs and 98% at 48 hrs (FIG. 4). Thus, the combination approach ablates p107 expression more rapidly and with higher efficiency than RNAi or PKO alone.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of reducing level of at least one target protein in a cell comprising the step of contacting the cell with a first agent and a second agent, wherein the first agent is an RNA interference (RNAi) molecule which reduces synthesis of the target protein, wherein the second agent is a chimeric polypeptide comprising a ubiquitin ligase polypeptide and a target protein interacting domain, wherein the ubiquitin ligase polypeptide is β-TrCP, wherein the target protein interacting domain is a polypeptide derived from papillomavirus E7, wherein the target protein is naturally-occurring or a mutant of Rb, p107, p130 or a combination thereof, wherein the first agent contacts the cell before, after or simultaneously with the second agent, and wherein the level of the target protein is reduced by greater than 90%.

2. The method of claim 1, wherein the RNAi molecule is a small interfering RNA (siRNA).

3. The method of claim 1, wherein the RNAi molecule is a small hairpin RNA (shRNA).

4. The method of claim 1, wherein the target protein interacting domain is E7N.

5. The method of claim 1, wherein the first agent and the second agent are in separate delivery vehicles.

6. The method of claim 1, wherein the first agent and the second agent are in a single delivery vehicle.

7. The method of claim 1, wherein the cell is a mammalian cell.

8. The method of claim 7, wherein the mammalian cell is a human cell or a murine cell.

9. The method of claim 1, wherein the method is used to treat or prevent a disease or condition in a subject.

10. The method of claim 9, wherein the method is used to treat or prevent cancer.

11. The method of claim 9, wherein the method is used to treat or prevent cardiovascular disease.

\* \* \* \* \*